United States Patent [19]

Skillin

[11] Patent Number: 4,846,831

[45] Date of Patent: Jul. 11, 1989

[54] MANUAL BACK-UP DRIVE FOR ARTIFICIAL HEART

[76] Inventor: David E. Skillin, 4816 Tula Ct., San Diego, Calif. 92122

[21] Appl. No.: 186,924

[22] Filed: Apr. 27, 1988

[51] Int. Cl.[4] .............................................. A61B 19/00
[52] U.S. Cl. ...................................... 623/3; 417/384; 417/389; 600/16
[58] Field of Search ................... 623/3; 417/903, 389, 417/384; 600/16, 18; 128/200.25, 200.29, 204.18, 204.28, 202.27, 205.13, 205.16, 205.15, 28, 30, 30.2

[56] References Cited

U.S. PATENT DOCUMENTS 4,449,524  5/1984  Gray ............................... 128/204.18
4,543,951  10/1985  Phuc ..................................... 128/911

OTHER PUBLICATIONS

Pp. 334, 335 of "Cardiovascular Care Handbook" (1986) by Springhouse Corporation, 1111 Bethlehem Pike, Springhouse, PA 19477.
"The Total Artificial Heart", pp. 1629-1636 of Gibbons' Surgery of the Chest (1983) W. B. Saunders Co. W. Washington Sq. Philadelphia, PA. 19105.
"Total Artificial Heart" pp. 466-487, (Sept. 1986, issue of Heart & Lung) C. V. Mosby Co., 11830 Westline Industrial Drive, St. Louis, Mo. 63146.

Primary Examiner—Richard J. Apley
Assistant Examiner—Stephanie L. Iantorno
Attorney, Agent, or Firm—Hill, Van Santen, Steadman & Simpson

[57] ABSTRACT

A manual back-up emergency drive device for air driven artificial hearts, particularly for the "Jarvik-7" heart, is adapted to be instantly connected to the air drive lines for the heart in the event of power and air pressure failures and manually actuated to sustain the life of the heart recipient during the power failure. The device includes a bellows type manually actuated pump with a pressure stroke and a suction stroke, and an air delivery tube emerging from the pump coupled to a pair of air tubes having quick disconnect coupling units on the ends thereof for mating with coupling units on the ends of the air drive tubes to the heart. The device also includes a metering valve in the tube serving the right ventricle of the heart, an instrument reading the metered and pumped air pressures pulsing through the system and a make-up air intake in the pump.

16 Claims, 2 Drawing Sheets

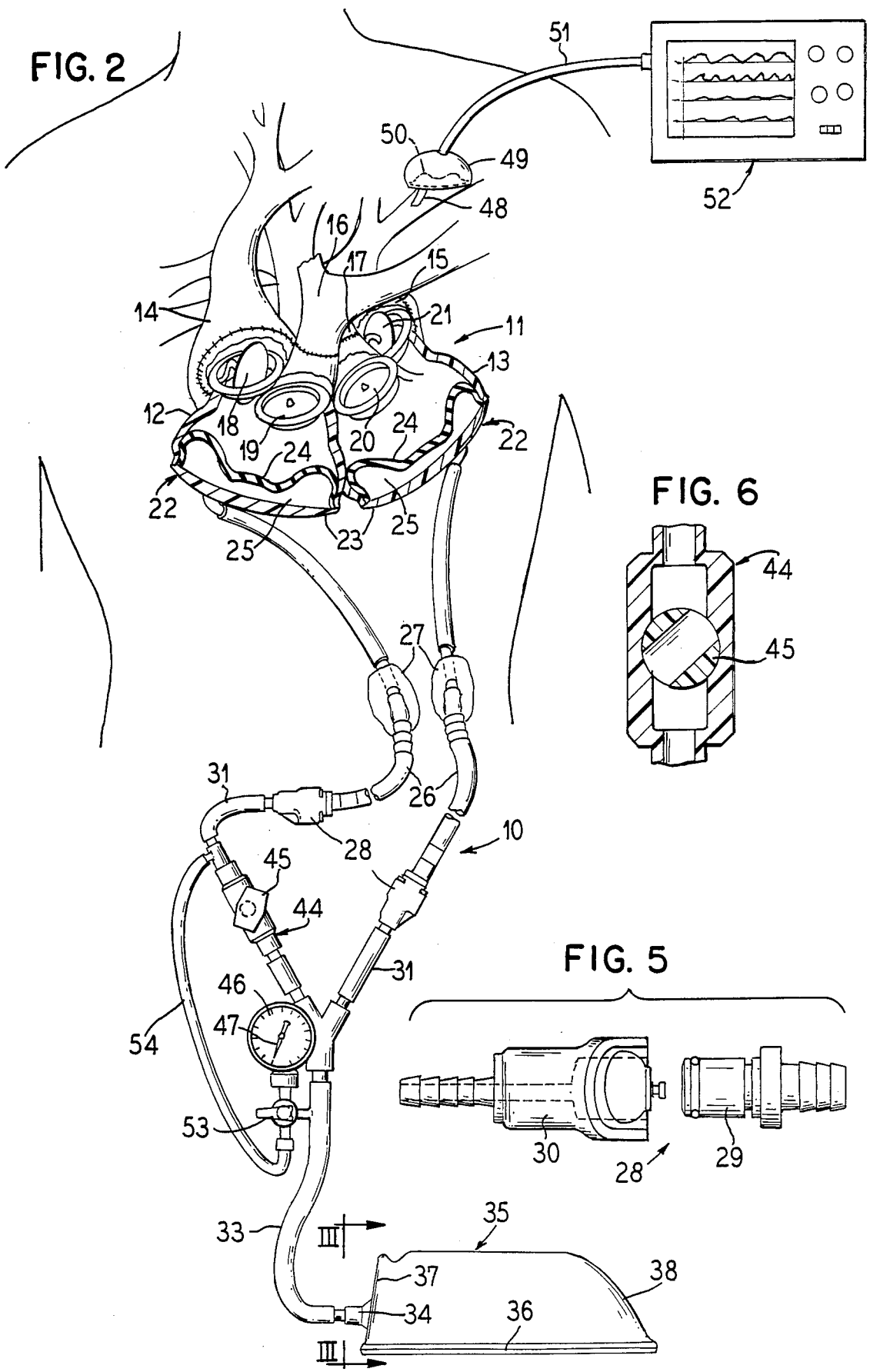

MANUAL BACK-UP DRIVE FOR ARTIFICIAL HEART

This invention relates to the art of sustaining life for wearers of artificial hearts and ventricular assist devices during power or air pressure failures and particularly deals with an emergency manually driven back-up device to operate "Jarvik-7" hearts during electric power or air pressure failure of the main drive unit for the heart.

BACKGROUND OF THE INVENTION

C.P.R. resuscitation procedures are useless to the wearers of artificial hearts which rely on an elaborate air drive system for proper functioning. These systems are power operated, requiring electrical input and even though they are equipped with emergency electric power back-up systems, such as batteries, there is always the danger of power outages of a sufficiently long duration to exhaust the back-up energy supply. Failure of the air power drive lines to the heart for even a short duration will be fatal to the patient.

It would therefore be a lifesaving improvement in artificial heart techniques to provide a device maintaining operation of the artificial heart during loss of power of the drive system for the heart and it would especially be an improvement in this art to provide such a device which can be immediately coupled to the air drive lines of the artificial heart and operated by any available attendant without requiring special skills or strength.

SUMMARY OF THE INVENTION

This invention will be specifically described for use with the presently successful "Jarvik-7" artificial heart. It should be understood, however, that the device is useful for any air driven artificial heart and ventricular assist devices.

The "Jarvik-7" artificial heart has pliable plastics material artificial ventricle bodies sewn to the atrial chambers of a human heart and the pulmonary and aortic arteries. These bodies carry diaphragm backed chambers having drive line tubes extending therefrom and emerging through the skin of the wearer to couple with air tubes from the drive console which is electrically powered and can sometimes be compacted for portability. The artificial ventricle units also carry artificial valves controlling oxygen depleted blood intake to the right atrial chamber and oxygen rich blood back to the body through the left ventricle chamber. During the deflation period of the diaphragms, blood flows from the atrial chamber into the ventricles and during the inflation period of the diaphragms, blood flows out of the ventricles to the arteries.

External air lines from the drive console are generally extended into the internal drive lines through Teflon-felt flange units on top of the skin of the wearer.

According to this invention the external end portions of the air drive lines have coupling components normally connected to the tubes from the drive console but also capable of being quickly coupled to the drive unit of this invention. This unit has mating coupling components on the ends of a pair of tubes which are connected through a "Y" connector tube to a pump tube. The pump tube emerges from a bellows type manually actuated pump modified to pulse air into and out of the pump tube to alternately flow and return the air to the diaphragm chambers to drive the heart.

The branch tube downstream from the "Y" connector leading to the drive line to the diaphragm chamber of the right artificial ventricle is equipped with a metering valve controlling flow therethrough for limiting systolic blood pressure within a desired maximum. The air tube feeding the drive line to the diaphragm chamber of the left artificial ventricle need not have such a restricting valve. The valve is preferably manually regulated to provide the desired air flow.

The pump tube and the air tube upstream from the metering valve preferably have a sphygmomanometer type instrument selectively connected thereto through a three way valve to indicate maximum and minimum pressure during manual operation of the pump.

It is also preferred to provide a monitoring instrument tapped into an artery of the patient for monitoring pulse rate, blood pressure, and rate change as is customary in monitoring heart patients.

A preferred pulsing pump is a foot actuated bladder-type pump with an air intake valve that closes on the pressure stroke. Normally such pumps are provided with check valves to build up pressure in the discharge tube. However, since the air driven artificial heart requires a pulsing of air flow to expand and retract the diaphragms, such a check valve is omitted so that air can flow back to the pump on the return stroke of the bladder and out of the pump on the compression stroke of the bladder. The air intake valve of the pump will admit additional air as required on the suction stroke but will, of course, close on the compression stroke. If desired, the rate of make-up air intake to the pump can be controlled by a manually set multi orifice unit.

The attached sheets of drawings show a preferred embodiment of the invention in which:

FIG. 2 is view, similar to FIG. 1 but illustrating the positions of the components on the suction stroke.

FIG. 5 is a side elevational view of the components of a tubular disconnect coupling for joining the drive unit of this invention to the air drive lines of the heart.

FIG. 6 is a enlarged longitudinal cross sectional view of the metering valve in the drive unit.

AS SHOWN ON THE DRAWINGS

Figures 1, 3, 4:
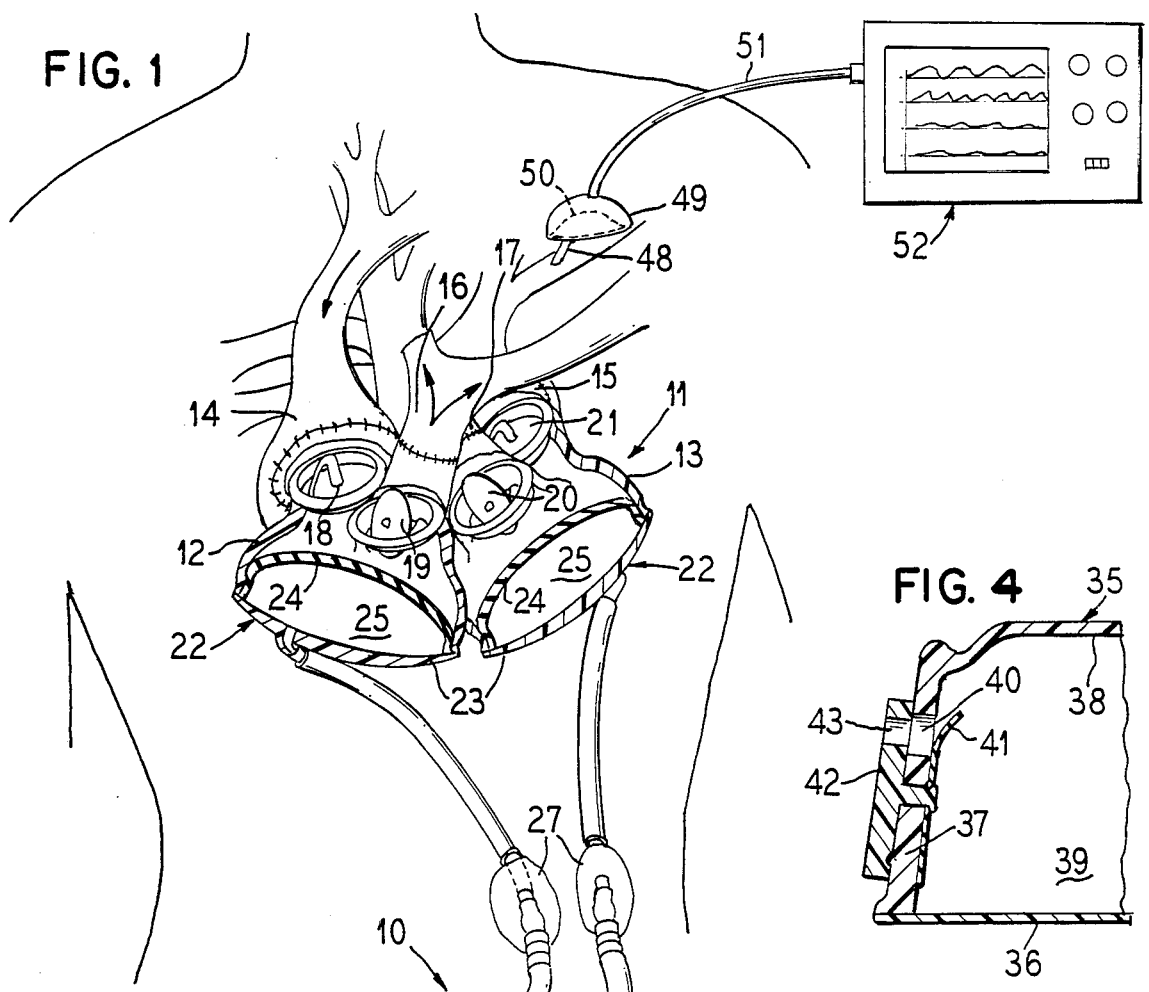
FIG. 1 is a diagrammatic fragmentary front view of a patient with an artificial heart implant shown partly in vertical section and having air drive lines extending externally of the body and detachably connected to the manual emergency drive of this invention and illustrating the positions of the components on the pressure stroke.
FIG. 3 is an end elevational view of the pump component of the drive taken along the line III—III of FIG. 2.
FIG. 4 is a cross-sectional view of the front end of the pump taken along the line IV—IV of FIG. 3.

The drive unit 10 of this invention is illustrated as connected to the air drive lines of a "Jarvik-7" heart implant 11 in the chest cavity of a living human recipient. The heart implant 11 includes artificial ventricles 12 and 13 sewn to the right and left atrial chambers 14 and 15 of the heart and also to the pulmonary and aortic arteries 16 and 17. Artificial valve implants 18–21 are provided to control blood flow into and out of the atrial chambers of the artificial ventricles. Each artificial ventricle supports a diaphragm unit 22 having a rigid backing 23 and an overlying flexible diaphragm 24 defining therebetween an air chamber 25 supplied with air through drive lines or tubes 26 emerging from the abdomen wall 27.

The external ends of these drive line tubes 26 are normally coupled to air lines from the drive consoles (not shown) through quick disconnect couplings 28. Each coupling as shown in FIG. 5, has a male and female component 29 and 30, respectively, carried by the ends of the external drive lines 26 and the air lines from the console (not shown).

The console normally monitors air flow into and out of the diaphragm chambers 25 of the right and left artificial ventricles 12 and 13 to expand the diaphragms on the compression stroke as illustrated in FIG. 1 and to collapse the diaphragms on the return or suction stroke as illustrated in FIG. 2. This alternate expansion and collapsing of the diaphragms causes the heart to function, pumping oxygen depleted blood into the lungs by the right ventricle and pumping oxygen rich blood back to the body by the left artificial ventricle with the valves 18-21 opening and closing in response to increase and decrease of pressures in the ventricles created by expansion and depression of the diaphragms.

According to this invention, in the event of failure of the console units controlling and monitoring the air flow to and from the diaphragm chambers 25, the manually actuated back-up emergency drive 10 of this invention is quickly brought into operation by opening and separating the quick disconnect couplings 28 to the console and reattaching the coupling components on the drive lines 26 to mating coupling components on the ends of air tubes 31. The opposite ends of these air tubes 31 are connected through a "Y" coupling 32 to a pump tube 33 emerging from the outlet nozzle 34 of a bladder or bellows type manually actuated air pump 35 (FIGS. 1-4). This pump 35 has a rigid base 36 and a rigid upstanding front wall 37. A rubber hood 38 has its periphery anchored and sealed to the base 36 and to the upstanding front wall 37. The air nozzle 34 receiving the tube 33 is open to the interior pumping chamber 39 under the hood 38. The front wall 37 has an air intake orifice 40 backed by a flap valve 41 in the chamber 39. A disc 42 pivoted on the outer face of the upstanding wall 37 has a plurality of different sized holes 43 therethrough adapted to be rotated into or out of alignment with the intake aperture 40 to control make-up air inflow into the pumping chamber 39 on the suction stroke.

The pump 35 can be conveniently manually operated by placing the base 36 on the floor and by alternately depressing and expanding the rubber boot 38 as by pressure from the foot F of an operator. The operator can thus easily collapse the boot 38 by stepping on it thereby forcing air trapped in the pumping chamber 39 out through the nozzle 34 and into the tube 33. Then upon lifting the foot off of the boot, the resilient boot will spring back to its free state condition drawing air back into the pumping chamber through the tube 33 and nozzle 34 and in the event there is insufficient air from the tube 34 to fill the pumping chamber 39, make-up air will enter the chamber through the orifice 40 and flap valve 41.

The air tube 31 connected to the drive line leading to the diaphragm chamber of the right ventricle is equipped with a metering valve 44 upstream from the "Y" connector 32.

This metering valve 44, as shown in FIG. 6, is adjustable by rotation of a plug 45 so as to bleed air at a desired rate to control maximum air pressure in the right ventricle chamber. The valve 44 may be fully closed so that air is delivered only to the left ventricle. This makes the device useful with ventricular assist devices for human hearts where air pressure drives the left ventricle to develop a desired blood pressure. For such usage the single open air tube 31 is coupled to a diaphragm drive chamber for the left ventricle of the heart to assist the human heart in developing blood pressure in the arteries.

The air pressure in the tube 31 downstream from the valve 44 is measured by an instrument such as a sphygmomanometer 46 having a needle 47. The valve 44 is adjusted so that the high pressure in the right ventricle chamber will not exceed a desired pressure for the blood.

An artery of the implant recipient can be tapped as indicated at 48 to a pressure sensitive transducer having a diaphragm chamber 49 covered by a flexible diaphragm 50 to flex the diaphragm and actuate drive fluid in a tube 51 to a monitoring instrument 52 which will visually show vital statistics of the operation of the heart such as blood pressure, pulse rate, rate change and the like. The manual actuation of the back-up drive 10 of this invention will, by its pressure and suction strokes, maintain the blood flow which is registered on the instrument the same as when the console drives the heart.

A three way valve 53 can be provided in the intake to the sphygmomanometer 46 so that air flow thereto can come from either the pump tube 33 through the tube 54, from the air tube 31 downstream from the valve 44 or shut off both intakes. It will be appreciated, of course, that other air flow indicating instruments including digital control readout devices could be substituted for this sphygmomanometer 46.

In operation it will be understood that alternate squeeze and release of the pump bladder 38 will maintain a pulsing of air into and out of the diaphragm chambers 25 to develop the desired pressure and pulse rates for driving the heart. A rhythmic squeezing and release of the pump bladder will maintain the operation of the heart in the same manner as the power driven console. The manual operation of the pump does not require much strength or energy and the operator can manually drive the pump for an extended period of time without fatigue. It will, of course, be understood that other types of manually actuated pumps, having pressure and suction strokes, could be used in the drive of this invention in place of the illustrated pump 35.

The preferred tubing 31 and 33 for the drive unit 10 is polyurethane but other flexible hose material is useful. The "Y" connector 32 and the metering valve 44 can be glass or plastic material.

From the above descriptions it will be understood that this invention provides an inexpensive foolproof manual back-up air drive device for air actuated artificial hearts and ventricular assist devices which requires only slight manual effort to maintain operation of the heart in the event of power failure.

I claim as my invention:

1. A back-up manual emergency drive for air driven artificial hearts of the type having artificial right and left ventricles carrying air propelled diaphragms fed from air drive lines actuating the diaphragms for pumping blood through the heart which comprises a manually actuated air pump having an air propelling stroke and an air return stroke, an air supply tube exiting from said pump, a "Y" connector adapted to join the supply tube to the air drive lines, a valve downstream from the "T" connector adapted to connect with the drive line to the right ventricle, manual means controlling flow through said valve to control the rate of air flow to the diaphragm of the right ventricle, and an instrument measuring air pressure in the air supply tube and in the drive tube downstream from the valve whereby manual operation of the stroke of the pump will drive the diaphragms for actuating the heart at a desired rate.

2. A manual back-up emergency drive for artificial hearts and ventricular assist devices of the type having diaphragms backed by air chambers for pumping blood through the heart and having air drive lines to the chambers which comprises a pump having a compression stroke and a return stroke for pulsing air, a pump air tube emerging from said pump, a "Y" connector tube having one arm connected to the pump air tube, a pair of air feed tubes connected to the other arms of the "Y" connector, a metering valve in one of the air feed tubes downstream from the "Y" connector, a pressure reading instrument connected to said air feed tube downstream from said metering valve and to the pump air tube for indicating the pulse rate and air pressure being delivered to said diaphragms, disconnect couplings adapted to join the pair of air feed tubes to the air drive lines, and an instrument connected to an artery of the patient wearing the heart to monitor blood conditions.

3. A unit for quick attachment through quick disconnect couplings to the air drive lines of artificial hearts which comprises a manually driven air pump having alternating pressure and suction strokes, an air tube emerging from said pump, a "Y" connector having one arm connected to the air tube, a pair of additional tubes each having an end connected to the other arms of the connector and opposite ends adapted to be attached through said couplings to the drive lines, a metering valve in one of the additional tubes, and an instrument actuated by air pressure downstream from the metering valve indicating the high and low air pressures pulsing through the tube as the pump is manually actuated.

4. The drive of claim 1 wherein the pump has an air intake valve to supply make-up air as needed by the air supply tube.

5. The drive of claim 1 wherein the instrument is a sphygmomanometer.

6. The drive of claim 1 including a monitoring instrument actuated by pressure developed by the heart in an artery of a patient with the heart implant to visually show the blood pressure, pulse and rate change.

7. The drive of claim 1 including a three-way valve controlling air flow to the instrument.

8. The drive of claim 1 wherein the manual means controlling flow through the valve is a rotatable plug with an orifice therethrough.

9. The drive of claim 2 wherein the pump is foot operated.

10. The drive of claim 2 wherein the pump has a resilient bellows hood.

11. The drive of claim 2 wherein the metering valve is adjustable.

12. The drive of claim 2 wherein one air feed tube is unrestricted.

13. The drive of claim 2 wherein the components are light weight and compact.

14. The drive of claim 3 including a monitoring device coupled to an artery downstream from the heart.

15. The device of claim 3 wherein each of the additional tubes has a quick disconnect coupling component affixed thereto.

16. The device of claim 2 wherein the metering valve may be completely closed and the other air feed tube coupled to a ventricular assist device so that all of the delivered air drives said device.

* * * * *